United States Patent
Berry

(10) Patent No.: US 11,395,588 B2
(45) Date of Patent: Jul. 26, 2022

(54) FIXATION DEVICE

(71) Applicant: SIMON BERRY OPTOMETRIST LTD, Gilesgate (GB)

(72) Inventor: Simon Berry, Gilesgate (GB)

( * ) Notice: Subject to any disclaimer, the term of this patent is extended or adjusted under 35 U.S.C. 154(b) by 127 days.

(21) Appl. No.: 17/048,595

(22) PCT Filed: Mar. 29, 2019

(86) PCT No.: PCT/GB2019/050919
§ 371 (c)(1),
(2) Date: Oct. 18, 2020

(87) PCT Pub. No.: WO2019/202294
PCT Pub. Date: Oct. 24, 2019

(65) Prior Publication Data
US 2021/0145272 A1 May 20, 2021

(30) Foreign Application Priority Data
Apr. 19, 2018 (GB) ..................................... 1806387

(51) Int. Cl.
*A61B 3/09* (2006.01)
*A61B 3/00* (2006.01)

(52) U.S. Cl.
CPC .............. *A61B 3/09* (2013.01); *A61B 3/0008* (2013.01); *A61B 3/0091* (2013.01)

(58) Field of Classification Search
CPC ....... A61B 3/09; A61B 3/0008; A61B 3/0091; A61B 3/113; B33Y 80/00
USPC ....................................................... 351/201
See application file for complete search history.

(56) References Cited

U.S. PATENT DOCUMENTS

| | | |
|---|---|---|
| 2006/0077349 A1 | 4/2006 | Kushida |
| 2008/0198330 A1* | 8/2008 | Taylor ................... A61B 3/112 351/221 |
| 2009/0303435 A1* | 12/2009 | Flitcroft ................ A61B 3/085 351/210 |
| 2015/0157199 A1 | 6/2015 | Sapiens |
| 2015/0313463 A1 | 11/2015 | Trumm |
| 2016/0270656 A1* | 9/2016 | Samec ................. A61B 3/0025 |
| 2017/0007119 A1 | 1/2017 | Cornsweet |

FOREIGN PATENT DOCUMENTS

| | | |
|---|---|---|
| EP | 3216386 A1 | 8/2019 |
| WO | 2008/120635 A1 | 10/2008 |
| WO | 2015/054672 A1 | 4/2015 |
| WO | 2017/111581 A1 | 6/2017 |

OTHER PUBLICATIONS

ISR; European Patent Office; NL; Jul. 3, 2019.
UK Search Report; Intellectual Property Office; Oct. 18, 2018.

* cited by examiner

*Primary Examiner* — Mohammed A Hasan
(74) *Attorney, Agent, or Firm* — Patshegen IP; Moshe Pinchas

(57) ABSTRACT

The present invention relates to aids or devices with optical elements which include a partially reflective surface, which allow examination or recordal of a patient who is fixated on a visual target, with said examination or recordal occurring along the same axis as the line of sight. The invention also allows for a target more personalised and customised to the patient's needs.

12 Claims, 4 Drawing Sheets

FIXATION DEVICE

TECHNICAL FIELD

The present invention relates to aids or devices with optical elements which allow examination, viewing or recordal of a patient who is fixated on a visual target, with said examination or recordal occurring along the same axis as the line of sight.

BACKGROUND

Visual accommodation or accommodative function is the ability of the eye to change its focus, achieved by the lens of the eye changing its shape, from distant to near objects (and vice versa). It is this adjustment of the optics of the eye that keeps an object in focus on the retina as its distance from the eye varies.

Abnormal accommodative function (accommodative lag or lead) occurs when there is a difference between accommodative demand and accommodative response. The measurement of accommodative function is a useful clinical measurement. Abnormal accommodative function is very common in patients with down syndrome (40%.) It is also found in patients with cerebral palsy, developmental delay and autism.

Traditionally, eye care professionals assess accommodative function by asking a patient to fixate on a suitable target and use a retinoscope to measure the accommodative response. The examination by the eye care professional is necessarily taken off axis from the patient's line of sight to avoid the target being obscured.

There are a number of challenges associated with this type of reading. Firstly, as the examination is occurring off the line of visual axis it is never entirely accurate. Further, it is difficult to be certain that the fixation target is holding the interest, and therefore the accommodative demand, of the patient. There are significant challenges when working with younger patients or patients with development disabilities for whom standard fixation targets hold limited interest.

It would be particularly useful to provide an aid or device to assist with visual fixation and which could allow a practitioner to examine, view or record along the same axis as the patient's line of sight.

Whilst the measurement of visual accommodation is of particular interest, the issue of being able to view a patient straight on i.e. along the same plane as their line of sight, whilst their attention or focus is held by a target of interest, would also be useful in other settings and in particular in clinical settings. The premise is particularly relevant for younger patients, and those with a learning disability. It would also be useful for tests such as cycloplegic refraction and for fundus photography, and OCT imaging and even when testing visual acuity. Even in settings such as dental exams, or ENT examinations, it would be useful to be able to view the patient 'face on' whilst allowing them to focus on a preferred target rather than the viewer. In fact, it would be useful in any clinical setting where the examination requires the patient to look directly at the clinician or recording device.

It is an object of the present invention to obviate or mitigate limitations associated with the prior art.

SUMMARY OF THE INVENTION

In accordance with the present invention there is provided a gaze fixation device for use in viewing a patient from an observation point, comprising:

an optical element comprising a partially reflective surface arranged such that, in use; incident light from a target is directed towards said surface and a first portion of said target incident light is transmitted through the surface, and a second portion of the target incident light is reflected from said surface at an angle offset from the angle of incidence; and incident light from the patient is directed towards said surface and a first portion of said patient incident light is transmitted through the surface, and a second portion of the patient incident light is reflected from said surface at an angle offset from the angle of incidence; such that the patient can view the target and can simultaneously also be viewed, via the optical element, from the observation point.

Advantageously, as the reflective surface acts as a beam splitter which changes the direction of a portion of the relevant incident light, the patient can simultaneously focus, along a plane, on the image of the target on the surface and themselves be viewed along the same plane. This is particularly useful as the target can be something that is of interest to the patient to increase the likelihood of fixation for a period of time, and the image of the patient that is presented to the viewer is effectively being viewed along the same plane which the patient is looking rather than being viewed from an angle. Effectively, the optical path of light entering the subject's eye and the optical path of light emitting from a patient's face are along the same plane for only part of their path.

The partially reflecting surface has a first side and an opposing side.

Preferably the incident light from the target is directed towards the first side of the partially reflecting surface and the incident light from the patient is directed towards the opposing side of said surface and a first portion of said patient incident light is transmitted through the surface, and a second portion of the patient incident light is reflected from the opposing side of said surface at an angle offset from the angle of incidence.

Preferably the optical element comprising a partially reflective surface is a partially reflecting, partially transmitting mirror or it is a beam splitter mirror.

Optionally the partially reflective surface reflects between 30% and 70% light and transmits between 30% and 70% light.

Optionally the partially reflective surface reflects between 40% and 60% light and transmits between 40% and 60% light.

Preferably the partially reflective surface reflects approximately 50% light and transmits approximately 50% light.

To clarify, the above refers to visible light.

It would be understood in the above that a portion of the light could be absorbed by the surface.

It is generally preferred that as much of the image light as possible is viewed by the patient via the optical device, however this must be balanced against the amount of light from the patient that is required to allow an appropriate view of the patient at the observation point.

It is preferred that the partially reflective surface is oriented at 45° to the plane of the incident light from the target so that the reflected light makes an angle of 90° to the incident light from the target.

Preferably the partially reflective surface comprises a partially metallised surface. This may be a partially silvered surface.

Alternatively, the partially reflective surface comprises a dichroic coating.

Optionally the gaze fixation device comprises a means for coupling to one or more optical instruments.

Such instruments may include fundus cameras and/or OCT and/or retinoscopes.

Preferably the gaze fixation device comprises a frame or housing.

Preferably the frame or housing holds the partially reflective surface in a fixed orientation.

Optionally the fixed orientation may be alterable.

Preferably the gaze fixation device comprises means for orienting the target with respect to the partially reflective surface.

Preferably the means for orienting the target with respect to the partially reflective surface is one or more structural elements for holding the target in a predetermined position and/or orientation relative to the partially reflective surface.

Optionally the one or more structural elements for holding the target in a predetermined position and/or orientation comprises a clamp for holding a target object.

The target object may be a mobile phone or tablet device, or a fixed target

It would however be understood that the target could be selected from almost any object or image that is meaningful or of interest to the patient.

Preferably the target object includes a light emitting element.

Optionally the target object may be associated with a light.

Optionally the gaze fixation device incorporates a means for illuminating the target.

The illumination of the target, either from within the target or by a source of illumination improves the ability of the patient to view the target via the partially reflective surface. As the patient will in fact be only viewing a portion of the light from the image (irrespective of whether they are viewing the reflected portion or the transmitted portion) it is preferable to have a well illuminated target.

Optionally the gaze fixation device includes one or more shield or shroud elements for preventing ingress of unwanted light to the partially reflective surface.

Optionally the incident light from a target may be directed or reflected onto the surface via one or more additional optical elements.

The one or more additional optical elements may be mirrors or partially reflective mirrors.

Advantageously, if the patient is positioned such that they are viewing a reflected image of the target, additional mirrors between the target and the partially reflective surface can be used to ensure the image is viewed in the expected orientation, i.e. without a reversed mirror image.

According to another aspect of the present invention there is provided a computer program that, when executed by a 3D printer, creates the patient fixation device described above. Optionally, the computer program, when executed by a 3D printer, creates the housing or frame of patient fixation device into which a partially reflective surface can be incorporated.

Various further features and aspects of the invention are defined in the claims.

BRIEF DESCRIPTION OF THE DRAWINGS

Embodiments of the present invention will now be described by way of example only with reference to the accompanying drawings where like parts are provided with corresponding reference numerals and in which.

DETAILED DESCRIPTION

Throughout this document a partially reflective surface is a surface that reflects light to a predetermined value and also transmits light to a predetermined value. A partially reflective mirror (also referred to as a partially reflecting mirror) or a beam splitter mirror is a mirror that allows a percentage of light to pass through it and a percentage of light to reflect off it. A partially reflective mirror or a beam splitter mirror can comprise a surface.

Viewing of a patient encompasses viewing by an individual or by a camera or device.

Figure 1:
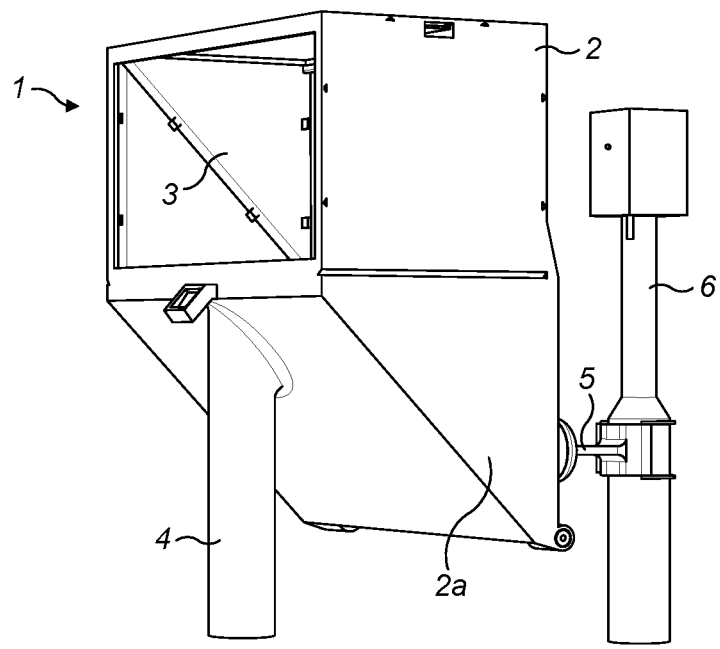
FIG. 1 is an image depicting a perspective view, from a first angle, of a device according to a first embodiment of the present invention.
Figure 2:
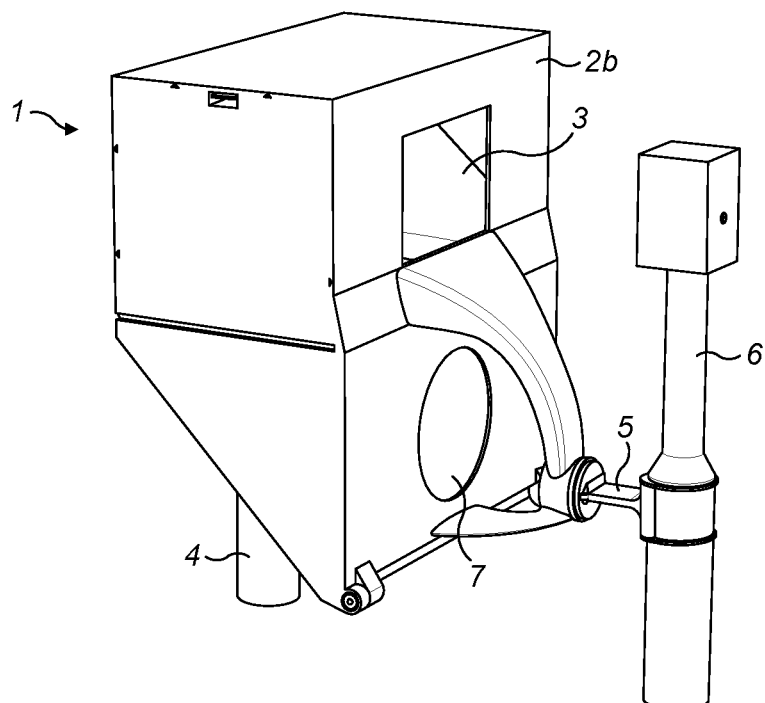
FIG. 2 is an image depicting a perspective view, from a second angle, of a device according to a first embodiment of the present invention.
Figure 3:
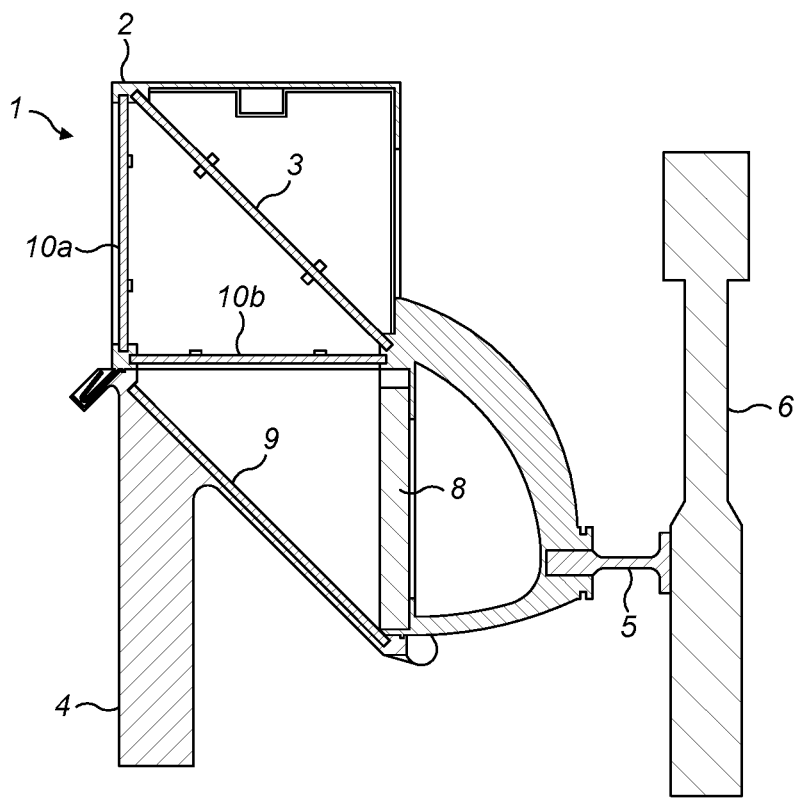
FIG. 3 is an image depicting a section view of a device according to a first embodiment of the present invention.
Figure 4:
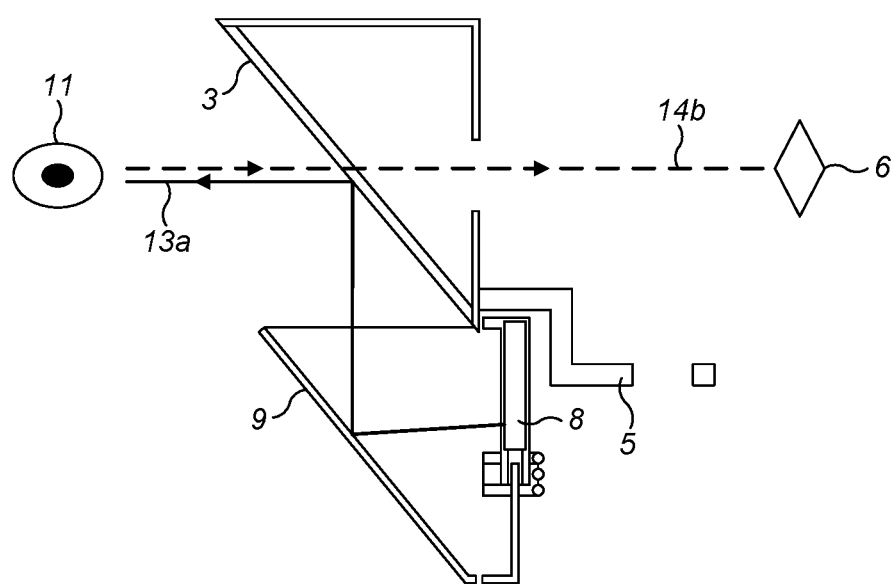
FIG. 4 in a line drawing depicting a section view of a device showing the 'viewed target image' path (solid line) and the 'viewed patient image path' (dashed line) according to a first embodiment of the present invention (reflected portions of light exist but are not shown)
Figure 7A:
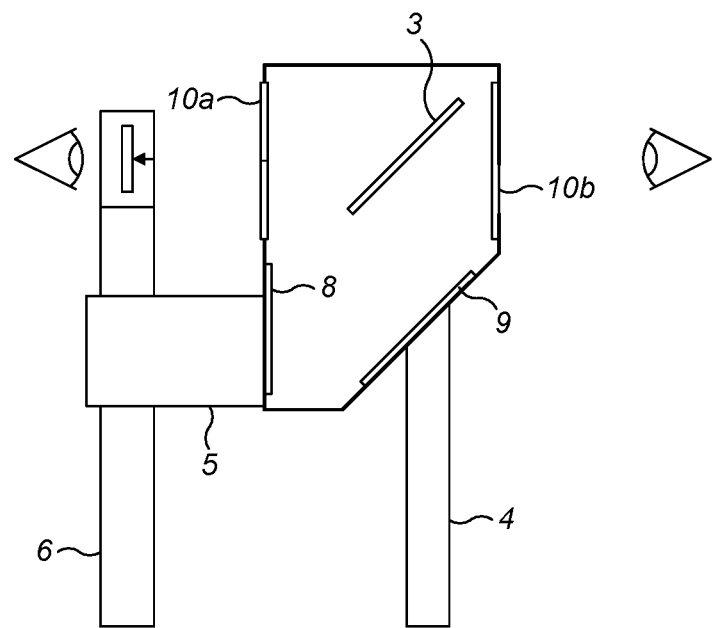
FIG. 7 shows an alternative variation of FIG. 3 where the optical instrument is held in either a fixed position (7a) or along a movable bracket (7b).
Figure 7B:
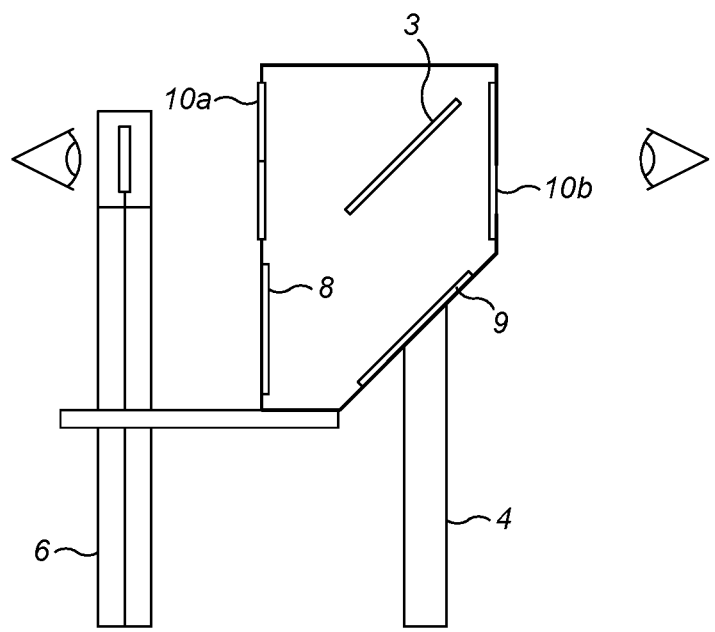

A first embodiment of the invention is generally depicted in FIGS. 1 and 2 which shows views of a patient fixation device 1 from various angles. This embodiment shows a handheld device which can be used by an optician when carrying out an examination, for example to determine the accommodative function of a patient. The device 1 can be combined with an additional optical instrument which in this case is a retinoscope 6, however it would be understood that it could be another instrument such as a fundus camera. The device 1 is provided with a housing 2 with a handle 4 extending from a lower surface thereof. As can be seen in FIGS. 1 and 2, but also in FIG. 3 (and FIGS. 7a and b) which shows the inside of the housing 2, the upper portion of the housing 2b contains a partially reflective mirror 3. In this embodiment the partially reflective mirror 3 is a layer of glass with a partially silvered layer thereon, however one skilled in the art would be aware of other appropriate means to produce the partially reflective mirror 3. The housing 2 also contains an area for receiving a target 8. In this case the lower portion of the housing 2a has a receiving section into which a mobile phone target 8 can be push fit. The housing is arranged such that the target 8 is held at a fixed orientation to the partially reflective mirror 3. The arrangement is such that the image from the target 8 is viewable by a patient 11 and the patient is viewable by a viewer 12 from an observation point. In this particular embodiment, an additional mirror 9 is provided within the housing such that the image from the target 8 is reflected by the mirror 9 towards the partially reflective mirror 3. FIG. 4 shows that the image is then split by the partially reflective mirror. In this embodiment, the partially reflective mirror is a 50R/50T mirror which acts as a beam splitter, however it would be understood that other levels of reflection and transmission could be used. In this case, 50% of the light from the image is reflected by the partially reflective mirror and is directed through a window 10 in the front of the housing 2 towards a patient and 50% of the image is transmitted through the mirror. As a significant portion is reflected, it can be seen by a patient who is looking at the front of the housing—the patient is effectively looking at the partially reflective mirror 3 and seeing the reflected image. In this case as the image has already been reflected by another mirror 9 it is also being seen in the expected orientation i.e. not as a mirror image. To clarify, the light is visible light.

At the same time that the patient is looking at the image of the target 8—effectively looking directly at the partially reflective mirror 3—a practitioner can look through an aperture at the 7 at the rear of the housing 2. In this case a practitioner can look via a retinoscope 6 which is secured to the housing 2 by a clamp 5. The patient can be seen through the partially reflective mirror 3 as again 50% of the light from the patient will be transmitted through the partially reflective mirror 3 and 50% will be reflected. The 50% which is transmitted through the partially reflective mirror 3 is on the same plane as the retinoscope so effectively the practitioner is viewing the image of the patient directly along their line of sight whilst the patient is focussing on an image from a target that is of interest to them.

Figure 5:
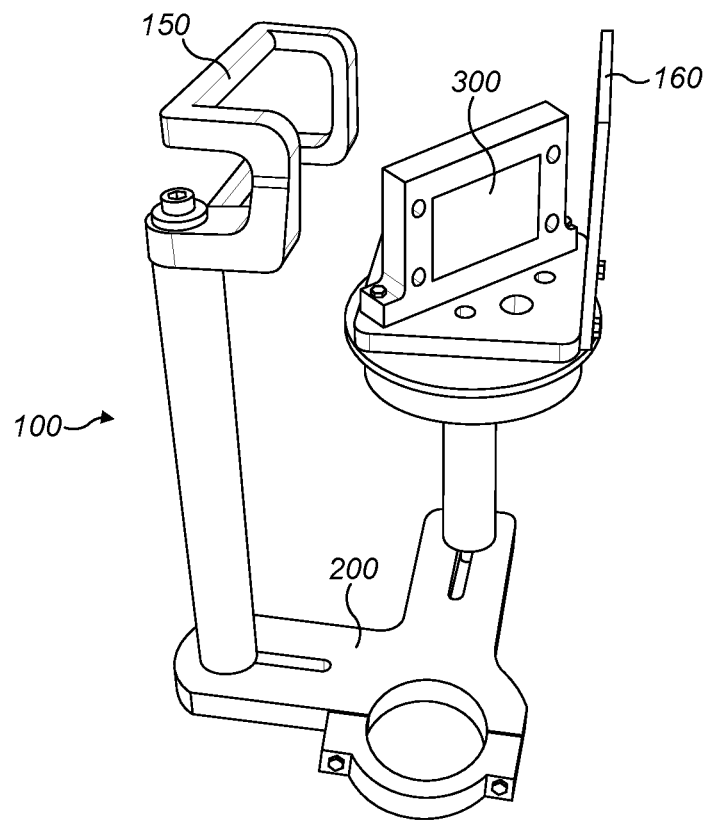
FIG. 5 is an image depicting a perspective view, of a device according to a second embodiment of the present invention.

Another embodiment of the present invention is also shown in FIG. 5. This embodiment is a desktop variant of a patient fixation device 100. The device 100 has a frame 200 which houses a partially reflecting mirror 300. As previously the partially reflective mirror 300 is a layer of glass with a partially metallised layer thereon, e.g. silver or aluminium, however one skilled in the art would be aware of other appropriate means to produce the partially reflective mirror 300. The frame 200 also has a portion, in this case a clamp 150, for holding a target 800 such as a mobile phone. It would however be understood that the target could be any target, and the frame simply includes an area where the target can be held or placed such it is correctly oriented with respect to the partially reflective mirror. The frame 200 is arranged with rigid portions that hold the target 800 at a fixed orientation to the partially reflective mirror 300. The arrangement is such that the image from the target 800 is viewable by a patient 110 and the patient is viewable by a viewer 120 from an observation point. In this version the partially reflective mirror is oriented at 45° to the plane of the incident light from the target so that the reflected light makes an angle of 90° to the incident light from the target—this reflected light is directed to the observation point. If the mirror is positioned at a different angle, the observation point would be along a different plane.

In some embodiments a camera can be placed at the observation point to record images of the patient, this can be in place of or in addition to direct viewing by a practitioner.

In this embodiment a shroud portion 160 can be included to prevent the ingress of unwanted light which may make the images more difficult to observe.

Typically, the device is not intended to be worn by the patient.

The embodiment may also be provided with a light (not shown) that can be used to further illuminate the target to improve visibility via the partially reflective mirror 300.

Figure 6:
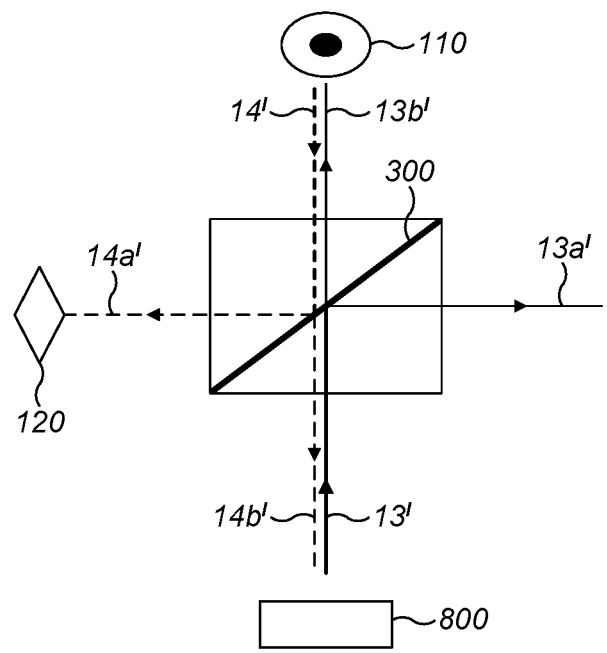
FIG. 6 is a simplified line drawing showing the 'viewed target image' path (solid line) and the 'viewed patient image path' (dashed line) according to an embodiment of the present invention.

As can be seen more clearly in FIG. 6, the beam splitting nature of the partially reflective mirror 300 acts such that a first portion of the light 13a' from the target 800 is reflected by the partially reflective mirror and a second portion 13b' of the light from the target is transmitted through the partially reflective mirror 300 towards a patient 110. Simultaneously, a first portion 14b' of the light from the patient will be transmitted through the partially reflective mirror 300 and a second portion 14a' will be reflected. The second portion 14a' which is reflected by the partially reflective mirror 300 is effectively a view of the patient 110 directly along their line of sight whilst the patient 110 is focusing on an image from a target that is of interest to them.

The amount of light reflected/transmitted by the partially reflective mirror is typically 50% and 50% i.e. 50R/50T. However, this can be altered to either reflect more or transmit more of the light, for example it could be 60% and 40%. Generally, a selection is appropriate providing there is sufficient light both reflected and transmitted to both view the target and view the patient, more of the light split to the examiner eases the clinical measurement but makes it more difficult for the patient to keep fixation and as such a balance must be found. In cases where the target is well lit or emits light it can be possible to direct more light to the examiner without causing problems with fixation. Typically, the mirror is selected to reflect between 30% and 70% of light.

Whilst the embodiments are described with respect to an optician, it would be understood that the device could be used to allow the direct face on visualisation of any patient. For example, a dentist may use it to allow a distressed patient, or a patient who finds it difficult to maintain focus, to fixate on something of interest to them whilst the dentist simultaneously has a view of the patient along the same plane as their line of sight.

All of the features disclosed in this specification (including any accompanying claims, abstract and drawings), from each of the embodiments and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It would also be understood that an individual may look to produce a device in accordance with the invention using 3D printing methodology. The invention thus also encompasses software, for example a CAD file, for instructing a 3D printer to print a patient fixation device according to the present invention. The software for instructing a 3D printer may be for instructing the printing of a frame or housing into which a partially reflecting mirror can then be introduced and held in a fixed orientation appropriate for the present invention.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

It will be appreciated that various embodiments of the present disclosure have been described herein for purposes of illustration, and that various modifications may be made without departing from the scope of the present disclosure.

In particular, in this case one skilled in the art would understand that various type of partially reflective mirror are available, including beam splitter cubes and partially metallised surfaces.

Further the frame or housing can be in various formats. The target may be varied depending on the preference of the patient.

Accordingly, the various embodiments disclosed herein are not intended to be limiting, with the true scope being indicated by the following claims.

The invention claimed is:

1. A handheld or desktop gaze fixation device for measuring accommodative function when viewing a patient from an observation point, comprising:
    an optical element comprising a partially reflective surface arranged such that, in use;
    incident light from a target is directed towards said surface and a first portion of said target incident light is transmitted through the surface, and a second portion of the target incident light is reflected from said surface at an angle offset from the angle of incidence; and
    incident light from the patient is directed towards said surface and a first portion of said patient incident light is transmitted through the surface, and a second portion of the patient incident light is reflected from said surface at an angle offset from the angle of incidence; and
    which comprises an area for receiving a personalised target, said target being an object of interest to the patient, and which has a means for orienting the target with respect to the partially reflective surface, said means for orienting being one or more structural elements for holding the target in a predetermined position and/or orientation relative to the partially reflective surface;
    wherein the partially reflective surface reflects between 30% and 70% light and transmits between 30% and 70% light, such that the patient can view the target and can is simultaneously viewable by an individual, via the optical element, from the observation point.

2. A gaze fixation device as in claim 1 wherein the partially reflecting surface has a first side and an opposing side and wherein the incident light from the patient is directed towards the opposing side of said surface and the first portion of said patient incident light is transmitted through the surface, and the second portion of the patient incident light is reflected from the opposing side of said surface at an angle offset from the angle of incidence.

3. A gaze fixation device as in claim 1 wherein the optical element comprising a partially reflective surface is a partially reflecting, partially transmitting mirror or a beam splitter mirror.

4. A gaze fixation device as in claim 1 wherein the partially reflective surface reflects approximately 50% light and transmits approximately 50% light.

5. A gaze fixation device as in claim 1 wherein the partially reflective surface is oriented at 45° to the plane of the incident light from the target so that the reflected light makes an angle of 90° to the incident light from the target.

6. A gaze fixation device as in claim 1 wherein the partially reflective surface comprises a partially metallised surface.

7. A gaze fixation device as in claim 1 wherein the partially reflective surface comprises a dichroic coating.

8. A gaze fixation device as in claim 1 which comprises a means for coupling to one or more optical instruments.

9. A gaze fixation device as in claim 1 which incorporates a means for illuminating the target.

10. A gaze fixation device as in claim 1 wherein the gaze fixation device includes one or more shield or shroud elements for preventing ingress of unwanted light to the partially reflective surface.

11. A gaze fixation device as in claim 1 wherein the device comprises one or more additional optical elements which may be mirrors or partially reflective mirrors.

12. A computer program that, when executed by a 3D printer, creates the patient fixation device of claim 1.

* * * * *